(12) United States Patent
Szarek

(10) Patent No.: US 10,137,029 B2
(45) Date of Patent: Nov. 27, 2018

(54) ANTI-SNORING DEVICE

(71) Applicant: Andrzej Szarek, Hayward, CA (US)

(72) Inventor: Andrzej Szarek, Hayward, CA (US)

( * ) Notice: Subject to any disclaimer, the term of this patent is extended or adjusted under 35 U.S.C. 154(b) by 0 days.

(21) Appl. No.: 15/783,286

(22) Filed: Oct. 13, 2017

(65) Prior Publication Data

US 2018/0104091 A1 Apr. 19, 2018

Related U.S. Application Data

(60) Provisional application No. 62/407,632, filed on Oct. 13, 2016.

(51) Int. Cl.
| | | |
|---|---|---|
| *A61F 5/56* | (2006.01) | |
| *G06F 3/16* | (2006.01) | |
| *H04R 1/02* | (2006.01) | |
| *H04R 29/00* | (2006.01) | |
| *A61M 21/02* | (2006.01) | |
| *A61M 21/00* | (2006.01) | |

(52) U.S. Cl.
CPC .............. *A61F 5/56* (2013.01); *A61M 21/02* (2013.01); *G06F 3/165* (2013.01); *H04R 1/028* (2013.01); *H04R 29/001* (2013.01); *A61M 2021/0011* (2013.01); *A61M 2021/0027* (2013.01); *A61M 2205/3375* (2013.01); *A61M 2205/52* (2013.01); *A61M 2205/8206* (2013.01); *H04R 2420/07* (2013.01)

(58) Field of Classification Search
CPC .......... A61F 5/56; A61F 13/2005; A61F 5/08; A61F 5/3707
See application file for complete search history.

(56) References Cited

U.S. PATENT DOCUMENTS

| | | | |
|---|---|---|---|
| 3,089,130 A | | 5/1963 | Wilson |
| 3,696,377 A | * | 10/1972 | Wall .......................... A61F 5/56 |
| | | | 128/204.23 |
| 4,644,330 A | | 2/1987 | Dowling |
| 4,788,533 A | | 11/1988 | Mequignon |
| 4,848,360 A | | 7/1989 | Palsgard et al. |
| 5,444,786 A | * | 8/1995 | Raviv ....................... A61F 5/56 |
| | | | 381/71.14 |
| 5,844,996 A | * | 12/1998 | Enzmann ............. A61B 5/7475 |
| | | | 381/71.6 |
| 2007/0102009 A1 | * | 5/2007 | Wong ....................... A61F 5/56 |
| | | | 128/898 |

(Continued)

*Primary Examiner* — Mohammad Islam
(74) *Attorney, Agent, or Firm* — Global Intellectual Property Agency, LLC; Daniel Boudwin

(57) ABSTRACT

An anti-snoring device. The anti-snoring device includes a housing having at least one sidewall. A speaker and a microphone are disposed on the sidewall. A memory is disposed within the housing, wherein the memory can store a plurality of audio files thereon. A microprocessor is disposed within the housing, the microprocessor having a logic that can receive an audio signal detected by the microphone, determine if the audio signal matches the sound of a human snoring within a pre-defined certainty, select one of the plurality of audio files stored on the memory, and play the selected audio file through the speaker between 40-50 dB. A power source is disposed within the housing, the power source in electrical communication with the microprocessor, the memory, the speaker, and the microphone.

16 Claims, 2 Drawing Sheets

(56) References Cited

U.S. PATENT DOCUMENTS

| | | | |
|---|---|---|---|
| 2007/0239225 A1* | 10/2007 | Saringer | A61F 5/56 607/42 |
| 2008/0310662 A1 | 12/2008 | Davidson et al. | |
| 2012/0163626 A1* | 6/2012 | Booij | G10K 11/178 381/92 |
| 2013/0204617 A1* | 8/2013 | Kuo | H04R 3/002 704/233 |
| 2014/0276227 A1* | 9/2014 | Perez | A61B 5/4818 600/586 |
| 2017/0100277 A1* | 4/2017 | Ke | A61F 5/56 |
| 2017/0150920 A1* | 6/2017 | Chang | A61B 5/4818 |
| 2017/0151085 A1* | 6/2017 | Chang | A61F 5/56 |
| 2017/0301337 A1* | 10/2017 | Golani | G10K 11/1782 |

* cited by examiner

US 10,137,029 B2

ANTI-SNORING DEVICE

CROSS REFERENCE TO RELATED APPLICATIONS

This application claims the benefit of U.S. Provisional Application No. 62/407,632 filed on Oct. 13, 2016. The above identified patent application is herein incorporated by reference in its entirety to provide continuity of disclosure.

BACKGROUND OF THE INVENTION

The present invention relates to anti-snoring devices. Specifically, the present invention relates to anti-snoring devices that play a selected audio file upon the detection of human snoring in order to disrupt a user's snoring without waking the user.

Many individuals suffer from snoring, which can frequently lead to feelings of inadequate sleep. Additionally, loved ones may also suffer from inconsistent sleep as the snorer can wake the loved ones with the volume of their snoring. Soft, soothing sounds similar to those a mother would make to her child, have been found to be effective in preventing snoring, while being insufficient to wake a sleeper. Many solutions in the known art can lead to the snorer being awoken when snoring occurs, further leading to feelings of exhaustion. Other solutions utilize harsh sounds that may not wake a user, but negatively affect the quality of the user's sleep. Therefore, a device that can disrupt a snoring person's sleep via soothing sounds without waking the snoring person is desired.

In light of the devices disclosed in the known art, it is submitted that the present invention substantially diverges in design elements from the known art and consequently it is clear that there is a need in the art for an improvement to existing anti-snoring devices. In this regard, the instant invention substantially fulfills these needs.

SUMMARY OF THE INVENTION

In view of the foregoing disadvantages inherent in the known types of anti-snoring devices now present in the prior art, the present invention provides an anti-snoring device wherein the same can be utilized for providing convenience for the user when preventing a user from snoring without disrupting sleep.

The present system comprises a housing having at least one sidewall, wherein a speaker is disposed on the sidewall. A microphone is further disposed on the sidewall. A memory is disposed within the housing, wherein the memory is configured to store a plurality of audio files thereon. A microprocessor is disposed within the housing, the microprocessor having a logic configured to receive an audio signal detected by the microphone, determine if the audio signal matches an audio file representing the sound of human snoring within a pre-defined certainty, select one of the plurality of audio files stored on the memory, and play the selected audio file through the speaker at a volume ranging between 40 and 50 dB. The system further comprises a power source disposed within the housing, wherein the power source is configured to provide power to the microprocessor, the memory, the speaker, and the microphone. In some embodiments, the plurality of audio files includes rhythmic pulsing sounds, wherein the rhythmic sounds are played at intervals. In another embodiment, the rhythmic sounds comprise the clicking of the human tongue. In other embodiments, the rhythmic sounds comprise the smacking of human lips. In yet another embodiment, the system further comprises a cord configured to electrically connect the power source to an external power source. In some embodiments, the system further comprises a switch configured to adjust the volume of sound played through the speaker. In another embodiment, the system further comprises a wireless transceiver in communication with the microprocessor, wherein the wireless transceiver is configured to wirelessly communicate with a remote device, such as a smartphone. In other embodiments, the memory is further configured to store data tracking the activity of the microprocessor thereon. In yet another embodiment, the system further comprises an activation button configured to selectively toggle the anti-snoring device between an activated state and a deactivated state. In some embodiments, the power source comprises a battery. In another embodiment, the battery is rechargeable.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
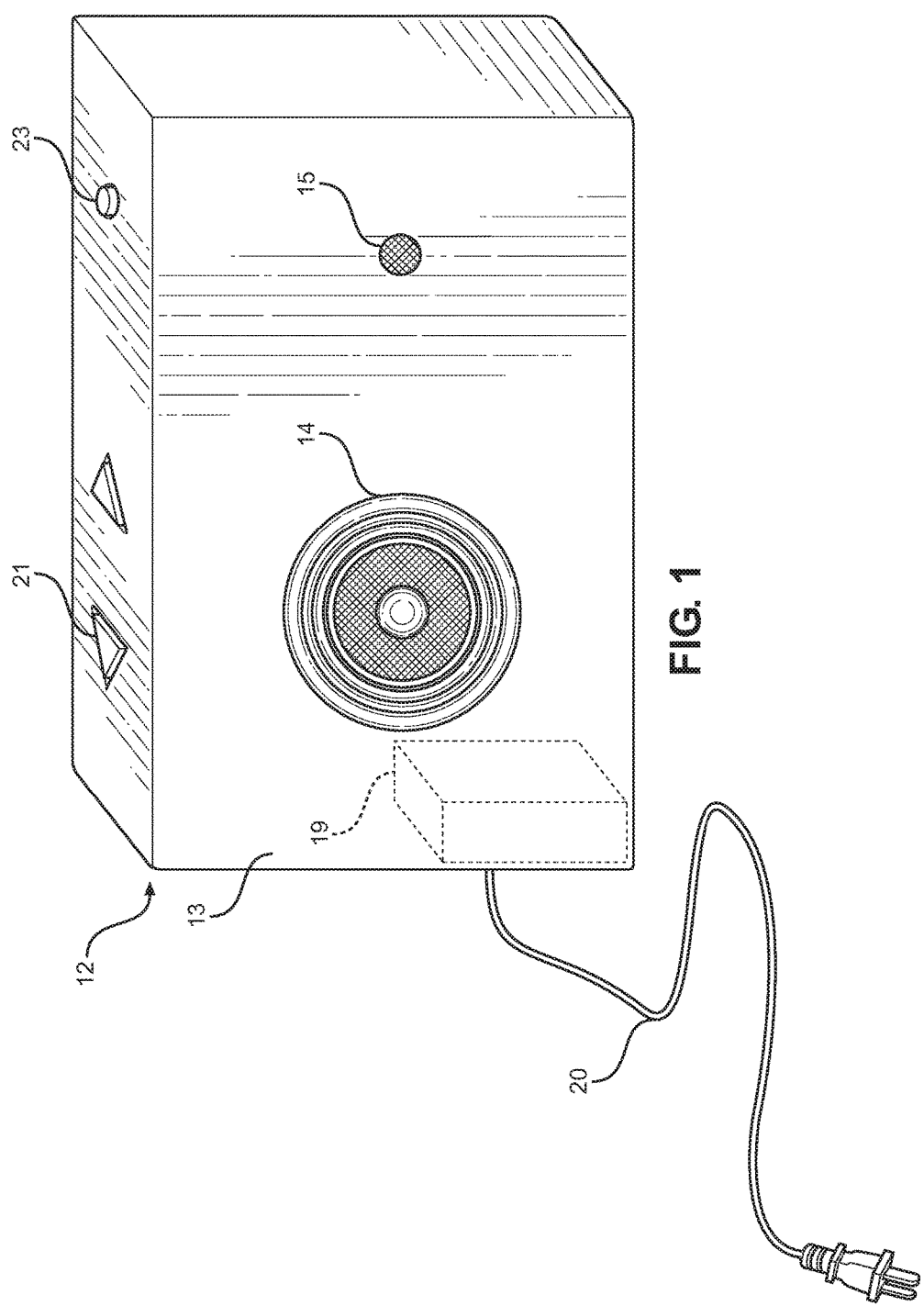
FIG. 1 shows a perspective view of an embodiment of the anti-snoring device.

Reference is made herein to the attached drawings. Like reference numerals are used throughout the drawings to depict like or similar elements of the anti-snoring device. The figures are intended for representative purposes only and should not be considered to be limiting in any respect.

Referring now to FIG. 1, there is shown a perspective view of an embodiment of the anti-snoring device. In the illustrated embodiment, the anti-snoring device comprises a housing 12 having at least one sidewall 13. A speaker 14 is disposed on the sidewall 13, wherein the speaker 14 is configured to emit sound therethrough. The speaker 14 is further configured to emit sound at a volume ranging between 40 and 50 dB, such that the anti-snoring device may be placed at a distance from the user while still functionally affecting the user. This particular decibel range allows the anti-snoring device to disrupt the snoring of a user, while still allowing the user to continue sleeping. A microphone 15 is disposed on the sidewall 13, wherein the microphone 15 is configured to receive an audio input from the vicinity of the housing 12. In this way, the microphone 15 functions as an audio sensor configured to detect the occurrence of snoring within the vicinity of the anti-snoring device. In the illustrated embodiment, the microphone 15 and the speaker 14 are disposed on the same sidewall 13, thereby allowing a user to position the housing 12 against a wall, while not interfering with the operation of the microphone 15 and the speaker 14. In the illustrated embodiment, a switch 21 is disposed on the sidewall 13, wherein the switch 21 is configured to adjust the volume of sound emitted from the speaker 14 within a pre-defined range. This pre-defined range is configured to prevent the sound emitted from the speaker 14 to reach a volume great enough to wake a sleeping user. In an alternate embodiment, the switch 21 comprises a sliding switch, rather than the pair of incremental switches depicted in the illustrated embodiment.

A power source 19 is configured to provide power to the electrical components and circuitry within the housing 12, including the speaker 14 and the microphone 15. In some embodiments, the power source 19 comprises a battery removably securable within the housing 12, wherein the battery is configured to allow the anti-snoring device to operate independently of an external power source for a period of time. In another embodiment, the battery is rechargeable, allowing a user to reuse the battery rather than replacing it, thereby reducing expenses to the user. In the illustrated embodiment, the anti-snoring device further comprises a cord 20 configured to operably connect to an external power source, such as a wall outlet or USB port, such that the cord 20 provides power to the anti-snoring device. In some embodiments, the cord 20 acts as the sole provider of power to the anti-snoring device, whereas in the illustrated embodiment, the cord 20 supplements the power source 19, allowing the anti-snoring device to draw off of external power to lengthen the life of the power source 19. In some embodiments, an activation button 23 is disposed on the housing 12, wherein the activation button is configured to selectively toggle the anti-snoring device between an activated and deactivated state. In this way, power is only provided to the device when in the activated state, allowing the user to preserve the lifetime of the power source 19 or minimize usage of an external power source via the cord 20, thereby minimizing expenses.

Figure 2:
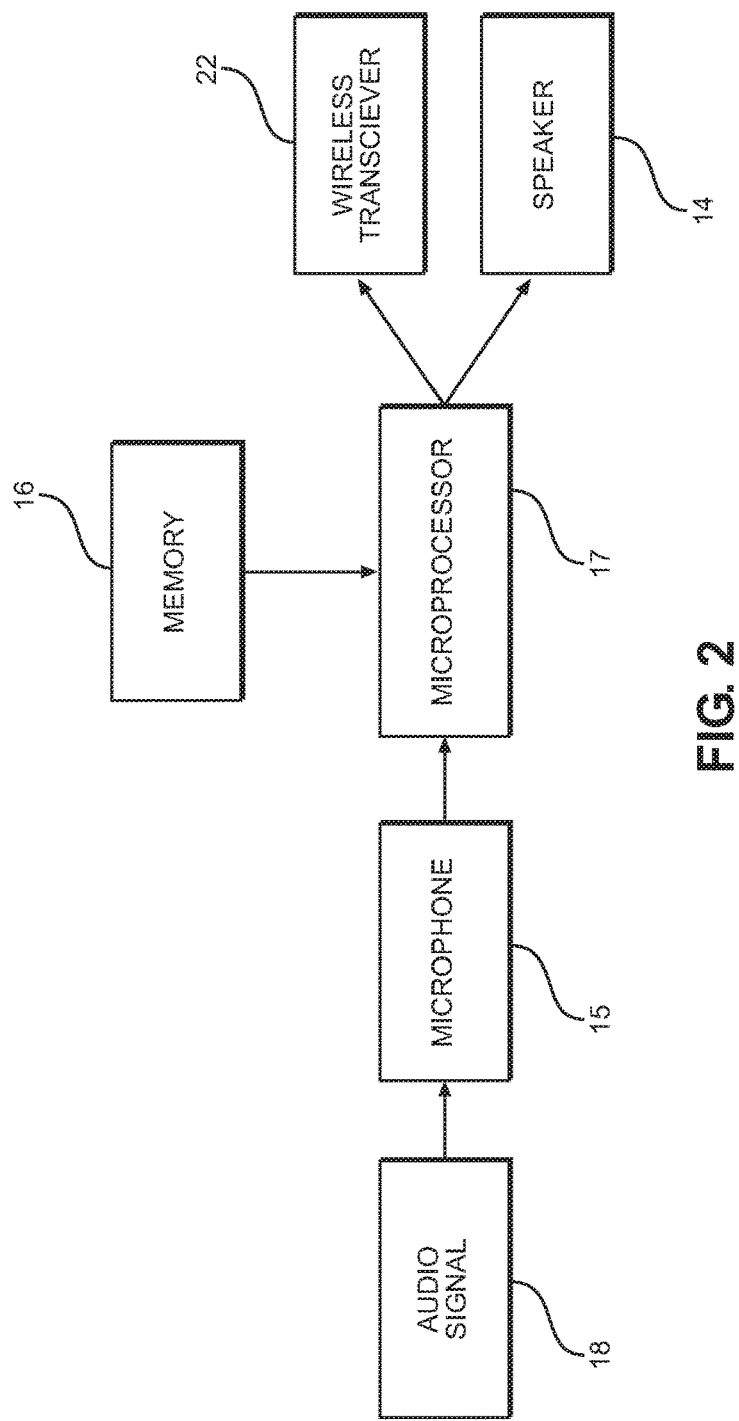
FIG. 2 shows a schematic view of an embodiment of the anti-snoring device.

Referring now to FIG. 2, there is shown a schematic view of an embodiment of the anti-snoring device. The anti-snoring device further comprises a memory 16 disposed within the housing, wherein the memory 16 is configured to store a plurality of audio files thereon. The plurality of audio files stored on the memory 16 comprise a first set of audio files and a second set of audio files, wherein the first set of audio files each represent various sounds of human snoring, such that the first set of audio files can be used for comparison against an audio signal 18 detected by the microphone 15. The second set of audio files represent rhythmic sounds configured to disrupt the snoring of a user when heard. In some embodiments, these sounds represent various soothing and calming sounds, including, but not limited to, a human tongue clicking, smacking and smooching sounds of human lips, and shushing noises. These sounds are selected for the soothing and calming effect of one human comforting another, much like a mother does for her child. The second set of audio files are configured to rhythmically sound at intervals for a set amount of time, such as, but not limited to, every 2 to 3 seconds, as the repetition of a pattern can further serve to prevent the waking of a user from sleep.

The anti-snoring device further comprises a microprocessor 17 disposed within the housing. The microprocessor 17 is configured to receive an audio signal 18, wherein the audio signal 18 is detected by the microphone 15. The microprocessor 17 then compares the audio signal 18 against the first set of audio files stored on the memory 16 disposed within the housing, wherein the audio file represents the sound of a snoring human. This comparison can include waveform analysis of the detected sound matched against the waveform of the sample sounds stored on the memory 16. Should the microprocessor 17 determine that the audio signal 18 matches the sound of human snoring within a pre-defined certainty, such as a confidence interval of 95 percent, the microprocessor 17 then selects one of the audio files of the second set of audio files stored on the memory 16 and plays the selected audio file through the speaker 14. In an alternate embodiment, the microprocessor 17 is configured to play the selected audio file when the microphone 15 detects a sound above a threshold noise level. In another embodiment, the threshold noise level can be adjusted, such that a user can select the volume of snoring required to trigger the audio file playing. In this way, the anti-snoring device can be calibrated for use with both heavy and light snorers. The selected audio file is configured to play for a set period of time, such that the snoring of the user can be disrupted. As the selected audio file is played at a volume between 40-50 dB, and comprises a rhythmic sound played at intervals, the snoring of the user can be disrupted without waking the user due to loud or randomly occurring sounds.

In the illustrated embodiment, the anti-snoring device further comprises a wireless transceiver 22. The wireless transceiver 22 is configured to wirelessly communicate with a remote device, such as a smartphone, tablet, or other electronic device. In this way, the user can receive data from the anti-snoring device regarding the usage of the anti-snoring device. This enables a user to determine the frequency of their snoring habits as determined by the number of times the microphone 15 detected snoring, allowing the user to gauge the effectiveness of the anti-snoring device. Additionally, the wireless transceiver 22 can transmit audio files to and from the remote device, allowing a user to use the remote device to detect snoring through the microphone of the remote device and play the audio files through the speakers of the remote device. In this way, the user can use the anti-snoring device remotely, such that the memory 16 and the computation of the microprocessor 17 are utilized while the detection and emission of sound are completed by the remote device.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:
1. An anti-snoring device, comprising:
 a housing having a front side, a rear side, and at least one sidewall extending therebetween;
 a speaker disposed on the front side of the housing;
 a microphone disposed on the front side of the housing;
 wherein the speaker and microphone are disposed on the front side such that the speaker and microphone are facing a same direction;
 a memory disposed within the housing;
 wherein the memory is configured to store a plurality of audio files thereon;
 a microprocessor operably connected to the memory;

a logic stored in the memory that, when executed by the microprocessor, causes the anti-snoring device to perform a method, the method comprising:
   receiving an audio signal detected by the microphone;
   determining if the audio signal matches one of a first set of audio files representing the sound of human snoring within a pre-defined certainty;
   selecting one of a second set of audio files stored on the memory; and
   playing the selected audio file of the second set of audio files through the speaker at a volume between 40-50 dB;
a power source disposed within the housing, wherein the power source is configured to provide power to the microprocessor, the memory, the speaker, and the microphone.

2. The anti-snoring device of claim 1, wherein the second set of audio files includes rhythmic sounds, wherein the rhythmic sounds are played at intervals.

3. The anti-snoring device of claim 2, wherein the rhythmic sounds comprise the clicking of the human tongue.

4. The anti-snoring device of claim 2, wherein the rhythmic sounds comprise the smacking of human lips.

5. The anti-snoring device of claim 1, further comprising a cord configured to electrically connect the power source to an external power source.

6. The anti-snoring device of claim 1, further comprising a switch configured to adjust the volume of sound played through the speaker.

7. The anti-snoring device of claim 1, further comprising a wireless transceiver in communication with the microprocessor, wherein the wireless transceiver is configured to wirelessly communicate with a remote device.

8. The anti-snoring device of claim 1, wherein the memory is further configured to store data tracking the activity of the microprocessor thereon.

9. The anti-snoring device of claim 1, further comprising an activation button configured to selectively toggle the anti-snoring device between an activated state and a deactivated state.

10. The anti-snoring device of claim 1, wherein the power source comprises a battery.

11. The anti-snoring device of claim 10, wherein the battery is rechargeable.

12. A method for preventing snoring comprising:
   detecting a sound with a microphone disposed on a front side of a housing;
   comparing the volume of the detected sound to a threshold volume stored on a memory disposed within the housing;
   wherein the threshold volume is adjustable via a threshold control disposed on the housing;
   activating a playback of an audio file stored on the memory if the detected sound exceeds the threshold volume;
   wherein the audio file is played through a speaker disposed on the front side in 2 to 3 second intervals until the volume of the detected sound falls below the threshold volume, and wherein the speaker faces the same direction as the microphone.

13. The anti-snoring device of claim 1, wherein the audio signal must exceed a volume threshold before the logic is executed.

14. The anti-snoring device of claim 13, wherein the housing further comprises a threshold control configured to selectively adjust the volume threshold required to execute the logic.

15. The anti-snoring device of claim 2, wherein the interval comprises between 2 to 3 seconds.

16. The anti-snoring device of claim 2, wherein the rhythmic sounds comprise a sound configured to sooth the user.

* * * * *